US007758880B2

(12) United States Patent
Hossainy

(10) Patent No.: US 7,758,880 B2
(45) Date of Patent: Jul. 20, 2010

(54) BIOCOMPATIBLE POLYACRYLATE COMPOSITIONS FOR MEDICAL APPLICATIONS

(75) Inventor: Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1846 days.

(21) Appl. No.: 10/815,421

(22) Filed: Mar. 31, 2004

(65) Prior Publication Data

US 2005/0169957 A1 Aug. 4, 2005

Related U.S. Application Data

(63) Continuation-in-part of application No. 10/317,435, filed on Dec. 11, 2002.

(51) Int. Cl.
*A61F 2/00* (2006.01)
(52) U.S. Cl. ........................................ 424/423; 424/422
(58) Field of Classification Search ........................ None
See application file for complete search history.

(56) References Cited

U.S. PATENT DOCUMENTS

| | | | |
|---|---|---|---|
| 2,072,303 A | 3/1937 | Herrmann et al. ........ 128/335.5 |
| 2,386,454 A | 10/1945 | Frosch et al. ................. 260/78 |
| 3,773,737 A | 11/1973 | Goodman et al. ............. 260/78 |
| 3,849,514 A | 11/1974 | Gray, Jr. et al. ............. 260/857 |
| 4,226,243 A | 10/1980 | Shalaby et al. ........... 128/335.5 |
| 4,329,383 A | 5/1982 | Joh ............................. 428/36 |
| 4,343,931 A | 8/1982 | Barrows ..................... 528/291 |
| 4,529,792 A | 7/1985 | Barrows ..................... 528/291 |
| 4,611,051 A | 9/1986 | Hayes et al. .............. 528/295.3 |
| 4,656,242 A | 4/1987 | Swan et al. ............... 528/295.3 |
| 4,733,665 A | 3/1988 | Palmaz ....................... 128/343 |
| 4,800,882 A | 1/1989 | Gianturco ................... 128/343 |
| 4,882,168 A | 11/1989 | Casey et al. ................. 424/468 |
| 4,886,062 A | 12/1989 | Wiktor ....................... 128/343 |
| 4,931,287 A | 6/1990 | Bae et al. .................... 424/484 |
| 4,941,870 A | 7/1990 | Okada et al. ................. 600/36 |
| 4,977,901 A | 12/1990 | Ofstead ...................... 128/772 |
| 5,019,096 A | 5/1991 | Fox, Jr. et al. ................. 623/1 |
| 5,100,992 A | 3/1992 | Cohn et al. ................. 424/501 |
| 5,112,457 A | 5/1992 | Marchant .................... 204/165 |
| 5,133,742 A | 7/1992 | Pinchuk ......................... 623/1 |
| 5,163,952 A | 11/1992 | Froix ............................. 623/1 |
| 5,165,919 A | 11/1992 | Sasaki et al. ................ 424/488 |
| 5,219,980 A | 6/1993 | Swidler ....................... 528/272 |
| 5,258,020 A | 11/1993 | Froix ............................. 623/1 |
| 5,272,012 A | 12/1993 | Opolski ..................... 428/423.1 |
| 5,292,516 A | 3/1994 | Viegas et al. ............... 424/423 |
| 5,298,260 A | 3/1994 | Viegas et al. ............... 424/486 |
| 5,300,295 A | 4/1994 | Viegas et al. ............... 424/427 |
| 5,306,501 A | 4/1994 | Viegas et al. ............... 424/423 |
| 5,306,786 A | 4/1994 | Moens et al. ............... 525/437 |
| 5,328,471 A | 7/1994 | Slepian ...................... 604/101 |
| 5,330,768 A | 7/1994 | Park et al. .................. 424/501 |
| 5,380,299 A | 1/1995 | Fearnot et al. ............. 604/265 |
| 5,417,981 A | 5/1995 | Endo et al. ................. 424/486 |
| 5,447,724 A | 9/1995 | Helmus et al. ............. 424/426 |
| 5,455,040 A | 10/1995 | Marchant .................... 424/426 |
| 5,462,990 A | 10/1995 | Hubbell et al. ............. 525/54.1 |
| 5,464,650 A | 11/1995 | Berg et al. ................... 427/2.3 |
| 5,485,496 A | 1/1996 | Lee et al. ..................... 378/64 |
| 5,516,881 A | 5/1996 | Lee et al. .................... 528/320 |
| 5,569,463 A | 10/1996 | Helmus et al. ............. 424/426 |
| 5,578,073 A | 11/1996 | Haimovich et al. ........... 623/1 |
| 5,584,877 A | 12/1996 | Miyake et al. ................ 623/1 |
| 5,605,696 A | 2/1997 | Eury et al. .................. 424/423 |
| 5,607,467 A | 3/1997 | Froix ............................. 623/1 |
| 5,609,629 A | 3/1997 | Fearnot et al. ................ 623/1 |
| 5,610,241 A | 3/1997 | Lee et al. .................... 525/411 |
| 5,616,338 A | 4/1997 | Fox, Jr. et al. .............. 424/423 |
| 5,624,411 A | 4/1997 | Tuch .......................... 604/265 |
| 5,628,730 A | 5/1997 | Shapland et al. ............. 604/21 |
| 5,644,020 A | 7/1997 | Timmermann et al. ...... 528/288 |
| 5,649,977 A | 7/1997 | Campbell ...................... 623/1 |
| 5,658,995 A | 8/1997 | Kohn et al. ................. 525/432 |
| 5,667,767 A | 9/1997 | Greff et al. ................ 424/9.411 |
| 5,670,558 A | 9/1997 | Onishi et al. ................ 523/112 |
| 5,674,242 A | 10/1997 | Phan et al. .................. 606/198 |
| 5,679,400 A | 10/1997 | Tuch .......................... 427/2.14 |
| 5,700,286 A | 12/1997 | Tartaglia et al. ............... 623/1 |

(Continued)

FOREIGN PATENT DOCUMENTS

EP 0 301 856 2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752 printed Aug. 25, 2003 (2 pages).

Aoyagi et al., *Preparation of cross-linked aliphatic polyester and application to thermo-responsive material*, Journal of Controlled Release 32:87-96 (1994).

(Continued)

Primary Examiner—Michael G Hartley
(74) Attorney, Agent, or Firm—Squire Sanders & Dempsey L.L.P.

(57) ABSTRACT

A composition is disclosed comprising a structural component comprising linear acrylic homopolymers or linear acrylic copolymers and a biobeneficial component comprising copolymers having an acrylate moiety and a biobeneficial moiety.

12 Claims, No Drawings

U.S. PATENT DOCUMENTS

| | | | |
|---|---|---|---|
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,735,897 A | 4/1998 | Buirge | 623/12 |
| 5,746,998 A | 5/1998 | Torchilin et al. | 424/9.4 |
| 5,759,205 A | 6/1998 | Valentini | 623/16 |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,854,376 A | 12/1998 | Higashi | 528/288 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | 424/489 |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A * | 8/2000 | Whitbourne et al. | 424/423 |
| 6,113,629 A | 9/2000 | Ken | 623/1.1 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | 424/423 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | 525/459 |
| 6,180,632 B1 | 1/2001 | Myers et al. | 514/252.1 |
| 6,203,551 B1 | 3/2001 | Wu | 606/108 |
| 6,211,249 B1 | 4/2001 | Cohn et al. | 514/772.1 |
| 6,214,901 B1 | 4/2001 | Chudzik et al. | 523/113 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | 514/234.8 |
| 6,248,129 B1 | 6/2001 | Froix | 623/1.42 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | 424/422 |
| 6,262,034 B1 | 7/2001 | Mathiowitz et al. | 514/44 |
| 6,270,788 B1 | 8/2001 | Koulik et al. | 424/423 |
| 6,277,449 B1 | 8/2001 | Kolluri et al. | 427/289 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | 604/265 |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | 424/400 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B2 | 11/2002 | Spada et al. | 514/311 |
| 6,494,862 B1 | 12/2002 | Ray et al. | 604/96.01 |
| 6,503,538 B1 | 1/2003 | Chu et al. | 424/497 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | 214/311 |
| 6,530,950 B1 | 3/2003 | Alvarado et al. | 623/1.13 |
| 6,530,951 B1 | 3/2003 | Bates et al. | 623/1.45 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,755 B2 | 7/2003 | Jackson et al. | 623/1.15 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,616,765 B1 | 9/2003 | Castro et al. | 118/500 |
| 6,623,448 B2 | 9/2003 | Slater | 604/95.01 |
| 6,625,486 B2 | 9/2003 | Lundkvist et al. | 604/21 |
| 6,645,135 B1 | 11/2003 | Bhat | 600/3 |
| 6,645,195 B1 | 11/2003 | Bhat et al. | 604/528 |
| 6,656,216 B1 | 12/2003 | Hossainy et al. | 623/1.13 |
| 6,656,506 B1 | 12/2003 | Wu et al. | 424/489 |
| 6,660,034 B1 | 12/2003 | Mandrusov et al. | 623/1.42 |
| 6,663,662 B2 | 12/2003 | Pacetti et al. | 623/1.13 |
| 6,663,880 B1 | 12/2003 | Roorda et al. | 424/423 |
| 6,666,880 B1 | 12/2003 | Chiu et al. | 623/1.11 |
| 6,673,154 B1 | 1/2004 | Pacetti et al. | 118/500 |
| 6,673,385 B1 | 1/2004 | Ding et al. | 427/2.28 |
| 6,689,099 B2 | 2/2004 | Mirzaee | 604/107 |
| 6,695,920 B1 | 2/2004 | Pacetti et al. | 118/500 |

| Patent/Publication | Date | Inventor | Class |
|---|---|---|---|
| 6,706,013 B1 | 3/2004 | Bhat et al. | 604/96.01 |
| 6,709,514 B1 | 3/2004 | Hossainy | 118/52 |
| 6,712,845 B2 | 3/2004 | Hossainy | 623/1.42 |
| 6,713,119 B2 | 3/2004 | Hossainy et al. | 427/2.25 |
| 6,716,444 B1 | 4/2004 | Castro et al. | 424/422 |
| 6,723,120 B2 | 4/2004 | Yan | 623/1.15 |
| 6,733,768 B2 | 5/2004 | Hossainy et al. | 424/426 |
| 6,740,040 B1 | 5/2004 | Mandrusov et al. | 600/439 |
| 6,743,462 B1 | 6/2004 | Pacetti | 427/2.24 |
| 6,749,626 B1 | 6/2004 | Bhat et al. | 623/1.1 |
| 6,753,071 B1 | 6/2004 | Pacetti | 428/212 |
| 6,758,859 B1 | 7/2004 | Dang et al. | 623/1.15 |
| 6,759,054 B2 | 7/2004 | Chen et al. | 424/423 |
| 6,764,505 B1 | 7/2004 | Hossainy et al. | 623/1.15 |
| 2001/0007083 A1 | 7/2001 | Roorda | 623/1.15 |
| 2001/0014717 A1 | 8/2001 | Hossainy et al. | 525/60 |
| 2001/0018469 A1 | 8/2001 | Chen et al. | 523/121 |
| 2001/0020011 A1 | 9/2001 | Mathiowitz et al. | 514/44 |
| 2001/0029351 A1 | 10/2001 | Falotico et al. | 604/103.02 |
| 2001/0037145 A1 | 11/2001 | Guruwaiya et al. | 623/1.15 |
| 2001/0051608 A1 | 12/2001 | Mathiowitz et al. | 514/44 |
| 2002/0005206 A1 | 1/2002 | Falotico et al. | 128/898 |
| 2002/0007213 A1 | 1/2002 | Falotico et al. | 623/1.21 |
| 2002/0007214 A1 | 1/2002 | Falotico | 623/1.21 |
| 2002/0007215 A1 | 1/2002 | Falotico et al. | 623/1.21 |
| 2002/0009604 A1 | 1/2002 | Zamora et al. | 428/450 |
| 2002/0016625 A1 | 2/2002 | Falotico et al. | 623/1.13 |
| 2002/0032414 A1 | 3/2002 | Ragheb et al. | 604/265 |
| 2002/0032434 A1 | 3/2002 | Chudzik et al. | 604/890.1 |
| 2002/0051730 A1 | 5/2002 | Bodnar et al. | 422/33 |
| 2002/0071822 A1 | 6/2002 | Uhrich | 424/78.37 |
| 2002/0077693 A1 | 6/2002 | Barclay et al. | 623/1.13 |
| 2002/0082679 A1 | 6/2002 | Sirhan et al. | 623/1.15 |
| 2002/0087123 A1 | 7/2002 | Hossainy et al. | 604/198 |
| 2002/0091433 A1 | 7/2002 | Ding et al. | 623/1.2 |
| 2002/0094440 A1 | 7/2002 | Llanos et al. | 428/421 |
| 2002/0111590 A1 | 8/2002 | Davila et al. | 604/265 |
| 2002/0120326 A1 | 8/2002 | Michal | 623/1.15 |
| 2002/0123801 A1 | 9/2002 | Pacetti et al. | 623/1.46 |
| 2002/0142039 A1 | 10/2002 | Claude | 424/486 |
| 2002/0155212 A1 | 10/2002 | Hossainy | 427/2.25 |
| 2002/0165608 A1 | 11/2002 | Llanos et al. | 623/1.45 |
| 2002/0176849 A1 | 11/2002 | Slepian | 424/93.7 |
| 2002/0183581 A1 | 12/2002 | Yoe et al. | 600/3 |
| 2002/0188037 A1 | 12/2002 | Chudzik et al. | 523/112 |
| 2002/0188277 A1 | 12/2002 | Roorda et al. | 604/523 |
| 2003/0004141 A1 | 1/2003 | Brown | 514/152 |
| 2003/0028243 A1 | 2/2003 | Bates et al. | 623/1.15 |
| 2003/0028244 A1 | 2/2003 | Bates et al. | 623/1.15 |
| 2003/0031780 A1 | 2/2003 | Chudzik et al. | 427/2.1 |
| 2003/0032767 A1 | 2/2003 | Tada et al. | 528/310 |
| 2003/0036794 A1 | 2/2003 | Ragheb et al. | 623/1.15 |
| 2003/0039689 A1 | 2/2003 | Chen et al. | 424/468 |
| 2003/0040712 A1 | 2/2003 | Ray et al. | 604/173 |
| 2003/0040790 A1 | 2/2003 | Furst | 623/1.11 |
| 2003/0059520 A1 | 3/2003 | Chen et al. | 427/2.1 |
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0113439 A1 | 6/2003 | Pacetti et al. | 427/2.24 |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0207020 A1 | 11/2003 | Villareal | 427/2.24 |
| 2003/0211230 A1 | 11/2003 | Pacetti et al. | 427/2.24 |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |
| 2004/0086542 A1 | 5/2004 | Hossainy et al. | 424/423 |
| 2004/0086550 A1 | 5/2004 | Roorda et al. | 424/448 |
| 2004/0096504 A1 | 5/2004 | Michal | 424/471 |
| 2004/0098117 A1 | 5/2004 | Hossainy et al. | 623/1.42 |

FOREIGN PATENT DOCUMENTS

| | | |
|---|---|---|
| EP | 0 396 429 | 11/1990 |
| EP | 0 514 406 | 11/1992 |
| EP | 0 623 354 | 11/1994 |
| EP | 0 665 023 | 8/1995 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| WO | WO 91/12846 | 9/1991 |
| WO | WO 94/09760 | 5/1994 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |

| WO | WO 03/082368 | 10/2003 |
| WO | WO 2004/009145 | 1/2004 |

OTHER PUBLICATIONS

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis($\alpha$-amino acid)$\alpha,\omega$-Alkylene Diesters, and Aliphatic Dicarboxylic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising $\alpha$-Amino Acid, 1,2-Ethanediol, and Adipic Acid*, Chemistry Letters, pp. 21-24, (1991).

van Beusekom et al., *Coronary stent coatings*, Coronary Artery Disease 5(7):590.596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Chung et al., *Inner core segment design for drug delivery control of thermo-responsive polymeric micelles*, Journal of Controlled Release 65:93-103 (2000).

\* cited by examiner

BIOCOMPATIBLE POLYACRYLATE COMPOSITIONS FOR MEDICAL APPLICATIONS

RELATED APPLICATIONS

This application is a Continuation-in-Part of U.S. patent application Ser. No. 10/317,435, filed on Dec. 11, 2002, which is incorporated herein by reference in its entirety.

BACKGROUND

1. Field of the Invention

This invention is directed to polymers used in medical applications, such as coatings for medical devices or implantable prostheses.

2. Description of the State of the Art

Among the many advances in medical practice in recent years is the development of medical devices that supplement the surgeon's skills. Examples of these are a variety of vascular catheters and guide wires that can be used to treat remote areas of the circulatory system otherwise available only by major surgery. Another is a stent, a device that retards restenosis after angioplasty. Another is the intra-ocular lens that restores youthful eyesight to the elderly afflicted with cataracts. Heart valves, artificial pacemakers, and orthopedic implants are among a lengthening list.

Nearly all of the above-described devices are constructed of plastics and metals that were never intended to invade, and sometimes reside for prolonged periods, in the human body. These devices present surfaces that bear little or no semblance to those of the human organs, which are generally hydrophilic, slippery, and obviously biocompatible. The penalty imposed on invasive devices that are not biocompatible is that they tend to be treated as foreign objects by the body's immune system. Inflammation and thrombosis often result.

The surface of devices already designed and manufactured from such materials can be made biocompatible, as well as hydrophilic and slippery, by properly designed coatings. Thus, the way has been opened to construct medical devices from conventional plastics and metals having the particular physical properties required, and then to apply suitable coatings to impart the desired properties to their surfaces.

In addition to improving the biocompatibility of the surface, polymers can be used to deliver biologically or pharmaceutically active agents to a treatment site. For example, stents have been modified with polymers for local application of a therapeutic substance. In order to provide an effective concentration at the treatment site, systemic administration of medication often produces adverse or toxic side effects for the patient. Local delivery is a preferred method of treatment, because smaller total levels of medication are administered in comparison to systemic dosages, and this medication is concentrated at a specific site. Local delivery thus produces fewer side effects and achieves better results. Briefly, a solution that includes a solvent, a polymer dissolved in the solvent, and a therapeutic substance dispersed in the blend is applied to the stent. The solvent is then allowed to evaporate, leaving on the stent surface a coating of the polymer and the therapeutic substance impregnated in the polymer. Once the stent has been implanted at the treatment site, the therapeutic substance is released from the polymer coating over time.

Although using coated stents improves pharmacological treatment of the patient and improves biocompatibility of the medical device in the patient, coatings can still be improved. In particular, it is desirable to have biologically beneficial (biobeneficial) stent coatings that are creep compliant and are capable of providing modulated drug release rate by increased water absorption in the overall coating. The embodiments of the present invention provide stent coatings that have these and other advantages.

SUMMARY

A composition is provided including a biologically compatible structural component such as a linear acrylic homopolymers, linear acrylic copolymers, or styrene and a biobeneficial component comprising copolymers having a bioactive or biobeneficial moiety. The biobeneficial component can also comprise an acrylate moiety. The composition can be used as a coating in medical applications such as for a stent. The composition can also be used for delivery of a drug or therapeutic substance. The mass ratio between the structural component and the biobeneficial component can be between about 99:1 and about 1:1, more narrowly, between about 19:1 and about 9:1, such as about 3:1. Examples of acrylic homopolymers and linear acrylic copolymers that can be used for making the structural component include poly(methylmethacrylate), poly(ethylmethacrylate), poly(n-propyl methacrylate), poly(isopropylmethacrylate), poly(n-butylmethacrylate), poly(n-laurylmethacrylate), poly(2-hydroxyethylmethacrylate), poly(methylmethacrylate-co-2-hydroxyethyl methacrylate), poly(n-butylmethacrylate-co-2-hydroxyethyl methacrylate), and mixtures thereof. One example of a copolymer comprising the biobeneficial component can be a block copolymer having the formula

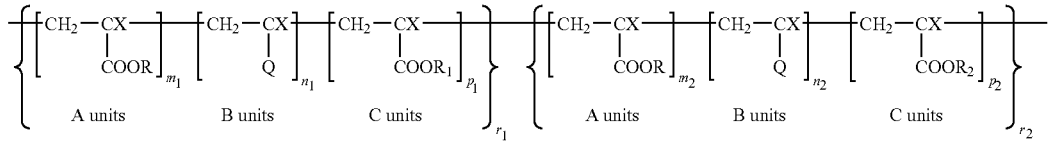

wherein $m_1$, $n_1$, $p_1$, $r_1$, $m_2$, $n_2$, $p_2$, and $r_2$ are all integers, wherein each of $m_1$, $m_2$, $p_1$, and $p_2$ can be 0 or greater; each of $n_1$, $n_2$, $r_1$, and $r_2$ can be greater than 0, and $r_1$ and $r_2$ can be the same or different; $m_1$ and $m_2$ can be the same or different; n, and $n_2$ can be the same or different; and $p_1$ and $p_2$ can be the same or different; X can be hydrogen or methyl group; each of R and $R_1$, independently, can be methyl, ethyl, n-propyl, iso-propyl, n-butyl, sec-butyl, iso-butyl, tert-butyl, lauryl, or 2-hydroxyethyl; and Q can be a fragment that provides the biobeneficial properties. Q fragments can be derived from poly(alkylene glycols), superoxide dismutate-mimetics (SODm), diazenium diolate-type nitric oxide donors, polycationic peptides, polysaccharides, pyrrolidone, vitamin E, sulfonated dextrane, β-phenoxyethanol, N,N-dimethylamino-2-ethanol, mannose-6-phosphate, sulfonic acid and derivatives of sulfonic acid, among others.

This invention also relates to a medical article fabrication method. The method comprises preparing a polymeric combination comprising a structural component including linear acrylic homopolymers or linear acrylic copolymers and a biobeneficial component comprising copolymers having an acrylate moiety and a biobeneficial moiety and forming a medical article from the combination or depositing the combination on a medical article. The biobeneficial component can include random, block, graft, or brush copolymers. One method of making block copolymers includes copolymerizing an acrylate and a biobeneficial monomer using of living, free-radical copolymerization with initiation-transfer-agent termination of the living chains.

DETAILED DESCRIPTION

Terms and Definitions

The following definitions apply:

The terms "block copolymer" and "graft copolymer" follow the terminology used by the International Union of Pure and Applied Chemistry (IUPAC). "Block copolymer" refers to a copolymer containing a linear arrangement of blocks. A block is defined as a portion of a polymer molecule in which the monomeric units have at least one constitutional or configurational feature absent from adjacent portions. "Graft copolymer" refers to a polymer composed of macromolecules with one or more species of blocks connected to the main chain as side chains, having constitutional or configurational features different than those in the main chain.

The term "AB-block copolymer" is defined as a block copolymer having moieties A and B arranged according to the general formula $-\{[A-]m-[B]n\}x-$, where each of m, n, and x is a positive integer, and m can be $\geq 2$, and n can be $\geq 2$.

The term "ABA-block copolymer" is defined as a block copolymer having moieties A and B arranged according to the general formula $-\{[A-]m-[B-]n-[A]p\}x-$, where each of m, n, p, and x is a positive integer, and m can be $\geq 2$, and n can be $\geq 2$, and p can be $\geq 2$.

The term "ABC-block copolymer" is defined as a block copolymer having moieties A, B, and C arranged according to the general formula $-\{[A-]m-[B-]n-[C]p\}x-$ where each of m, n, p, and x is a positive integer, and m can be $\geq 2$, and n can be $\geq 2$, and p can $\geq 2$.

These blocks need not be linked at the ends, since the values of the integers determining block length ensure that the individual blocks are polymers in their own right. Accordingly, the ABA-block copolymer can be named poly A-block-co-poly B-block-co-poly A-block copolymer, the ABC-block copolymer can be named poly A-block-co-poly B-block-co-poly C-block co-polymer and the AB-block co-polymer can be named poly A-block-co-poly B-block copolymer. Blocks A, B, and C can be longer than three blocks and can be alternating or random.

Note that the term "copolymer" encompasses for purposes of this disclosure a polymer with two or more constituent monomers and does not imply a polymer of only two monomers.

The term "brush copolymer" includes two copolymer types. The first type includes co-polymers with some branch points with, in some embodiments, functionality greater than three. The second type includes the following structure:

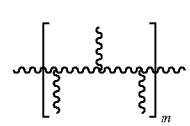

Structure I

In Structure I, the horizontal chain symbolizes the polymer backbone chain, for example, a poly(n-butyl methacrylate) chain, and vertical chains symbolize side chains connected to the backbone chain. One example of a polymer that can form side chains is poly(ethylene glycol).

A "linear polymer" is a polymer that does not contain branches with a chain length greater than 3.

In some embodiments, a thermoplastic polymer is a polymer that may not be capable of forming cross-links, and consequently does not form crosslinks when heated, whether with or without a crosslinking catalyst. A thermoplastic polymer that includes cross linking fragments can be crosslinked. Examples of such fragments include π-bonds and functional groups, such as amino, epoxy, urethane, etc. Non crosslinking thermoplastic polymers soften and fuse when heated and solidify when cooled. This melt-freeze cycle can be repeated many times without substantially chemically altering the polymer. Also, a solvent-soluble thermoplastic polymer remains soluble after any number of melt-freeze cycles.

Polymers that are linear and thermoplastic are "linear thermoplastic polymers." For the purposes of the present application, whenever the terms "linear polymer," or "thermoplastic polymer," or "linear thermoplastic polymer" are used, in some embodiments these terms specifically exclude polymers that contain crosslinks. In some embodiments, "linear polymers" and "thermoplastic polymers" are substantially free of crosslinked fragments; in some embodiments, completely free of crosslinked fragments.

Embodiments

According to embodiments of the present invention, the composition can include a structural component comprising linear acrylic homopolymers or copolymers or styrene, which, in some embodiments can be thermoplastic; and a biobeneficial component comprising copolymers having an acrylate moiety and a biobeneficial or bioactive moiety. The structural component and the biobeneficial component can be blended. In some embodiments, the two components can be bonded, linked such as by a linking agent, conjugated or cross-linked. The mass ratio between the structural component and the biobeneficial component can be between about 99:1 and about 1:1, more narrowly, between about 19:1 and about 9:1, for example, about 3:1. In the biobeneficial component, the mass ratio between the acrylate moiety and the biobeneficial moiety can be between about 99:1 and about 1:1, more narrowly, between about 19:1 and about 9:1, for example, about 3:1.

Structural Component

The biologically compatible structural component can comprise linear acrylic homopolymers or copolymers, for example. In some embodiment, the homo- and co-polymers can be thermoplastic. The structure of linear acrylic homopolymers and copolymers can be illustrated by general Formula I.

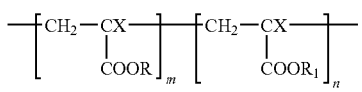

Formula I $$\left[ CH_2-CX \atop COOR \right]_m \left[ CH_2-CX \atop COOR_1 \right]_n$$

wherein X can be hydrogen or methyl group; each of R and $R_1$ can independently be methyl, ethyl, n-propyl, iso-propyl, n-butyl, sec-butyl, iso-butyl, tert-butyl, lauryl, or 2-hydroxyethyl; m is a positive integer, and n can be 0 or a positive integer. If n=0, the polymer represented by Formula I is an acrylic homopolymer, and if n≠0, the polymer represented by Formula I is an acrylic copolymer.

A linear acrylic homopolymer corresponding to Formula I can be obtained by polymerizing one acrylic monomer, $CH_2$=CX-M, using common techniques. To obtain a linear acrylic copolymer corresponding to Formula I, two or more acrylic monomers, $CH_2$=CX-M, can be co-polymerized. Any combination of acrylic monomers can be used to prepare a linear acrylic co-polymer according to Formula I. Examples of $CH_2$=CX-M monomers that can be used are shown in Table 1.

suitable for the structural component include poly(methylmethacrylate-co-2-hydroxyethyl methacrylate) (PMMA-HEMA) and poly(n-butylmethacrylate-co-2-hydroxyethyl methacrylate) (PBMA-HEMA). Other homopolymers or copolymers described by Formula I, or mixtures thereof can be also used.

Biobeneficial Component

The biobeneficial component can comprise a copolymer having at least one acrylate moiety and at least one biobeneficial moiety. In some embodiments, random, block, graft or brush copolymers can be used. For random copolymers, some constituent units of the copolymers can include an acrylate moiety while other constituent units can include a biobeneficial moiety.

Examples of useful block copolymers include AB-, ABA-, BAB-, ABC-, or ABCBA block copolymers. For AB-, ABA- or BAB-block copolymers, either moiety A or B can be an acrylate moiety, and the other moiety can be a biobeneficial moiety. Similarly, for an ABC block copolymer, either moiety

TABLE 1

| No. | Monomer | Abbreviation | X | M |
|---|---|---|---|---|
| 1 | Methylmethacrylate | MMA | $CH_3$ | $-C(=O)-O-CH_3$ |
| 2 | Ethylmethacrylate | EMA | $CH_3$ | $-C(=O)-O-CH_2-CH_3$ |
| 3 | n-Propyl methacrylate | PMA | $CH_3$ | $-C(=O)-O-CH_2-CH_2-CH_3$ |
| 4 | iso-Propylmethacrylate | i-PMA | $CH_3$ | $-C(=O)-O-CH(CH_3)-CH_3$ |
| 5 | n-Butylmethacrylate | BMA | $CH_3$ | $-C(=O)-O-CH_2-CH_2-CH_2-CH_3$ |
| 6 | n-Laurylmethacrylate | LMA | $CH_3$ | $-C(=O)-O-(CH_2)_{11}-CH_3$ |
| 7 | 2-Hydroxyethyl-methacrylate | HEMA | $CH_3$ | $-C(=O)-O-CH_2-CH_2-OH$ |

One example of a linear acrylic homopolymer suitable for the structural component is poly(n-butyl methacrylate) (PBMA). The structure of PBMA corresponds to Formula I, where X=$CH_3$, R=n-$C_4H_9$, and n=0. PBMA is a thermoplastic homopolymer. Examples of linear acrylic copolymers A, B, or C, or any two of A, B, and C can be an acrylate moiety or moieties, while the remaining moiety or moieties can be biobeneficial.

One example of a block copolymer that can be used is illustrated by Formula II:

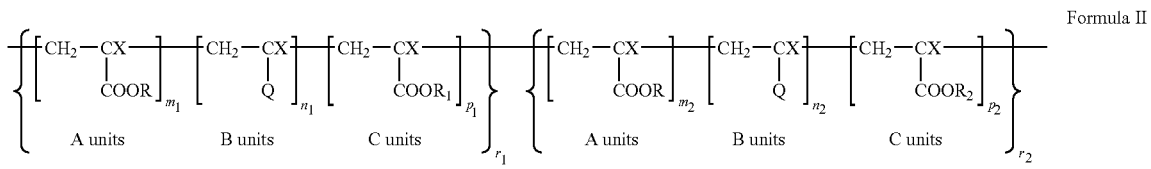

Formula II wherein:

(a) $m_1$, $n_1$, $p_1$, $r_1$, $m_2$, $n_2$, $p_2$, and $r_2$ are all integers, wherein $m_1 \geq 0$, $n_1 > 0$, $p_1 \geq 0$, $r_1 > 0$; $m_2 \geq 0$, $n_2 > 0$, $p_2 \geq 0$, $r_2 > 0$; and if $m_1 = 0$, then $p_1 > 0$, and if $p_1 = 0$, then $m_1 > 0$; and if $m_2 = 0$, then $p_2 > 0$, and if $p_2 = 0$, then $m_2 > 0$; and $r_1$ and $r_2$ can be the same or different; $m_1$ and $m_2$ can be the same or different; $n_1$ and $n_2$ can be the same or different; and $p_1$ and $p_2$ can be the same or different;

(b) X can be hydrogen or methyl group;

(c) each of R and $R_1$ can be methyl, ethyl, n-propyl, iso-propyl, n-butyl, sec-butyl, iso-butyl, tert-butyl, lauryl, 2-hydroxyethyl; and (d) B-units are biobeneficial moieties, which can be attached to the backbone of the block copolymer in a variety of ways, for example by an acyl group or by a methylene bridge. Q makes the B-units biobeneficial, If a random copolymer is used as the biobeneficial component, the structure of the random copolymer is generally similar to the structure shown in Formula II, except the A-, B-, and C-units in the random copolymer are randomly distributed.

Examples of Q providing biobeneficial properties to the B-units include those derived from poly(alkylene glycols) such as poly(ethylene glycol), poly(propylene glycol), poly(tetramethylene glycol), poly(ethylene glycol-co-propylene glycol), or poly(ethylene oxide-co-propylene oxide), superoxide dismutate-mimetics (SODm), diazenium diolate type nitric oxide donors, polycationic peptides, polysaccharides, for example, heparin or heparin derivatives, pyrrolidone, vitamin E, sulfonated dextrane, β-phenoxyethanol, N,N-dimethylamino-2-ethanol, mannose-6-phosphate, sulfonic acid and derivatives of sulfonic acid such as propanesulfonic acid, 2-methyl-1-propanesulfonic acid, benzenesulfonic acid, and 3-methoxy-2-hydroxypropanesulfonic acid.

Superoxide dismutate-mimetics (SODm) are oxidoreductase-based complexes that contain of copper, iron, or manganese cations. SODm are major intracellular enzymes that protect the cell from oxygen toxicity by dismutating the superoxide, radical $O_2^-$, to oxygen and hydrogen peroxide. A hepta coordinated, manganese-based SODm, manganese (II) dichloroaminoethylthiolated pentaazatetracyclohexacosatriene (SOD-40470) (manufactured by Metaphore Pharmaceuticals, Inc., St. Louis, Mo.) is one example of SODm that can be used in B-units. Other types of SODm can also be used, if desired.

Diazeniumdiolate-type nitric-oxide donors are adducts of nitric oxide (NO) with nucleophilic amines. Diazenium diolates, also known as NONOates, are highly biologically compatible and possess valuable medicinal properties. In slightly acidic medium, they spontaneously release NO, which has excellent therapeutic properties. One example of diazenium diolate that can be used for making B-units is an aliphatic NONOate, 1,3-propanediamine, N-{4-[1-(3-aminopropyl)-2-hydroxy-2-nitrosohydrazino]butyl}-diazen-1-ium-1,2-diolate, also known as speramine diazenium diolate (SDD) and having the formula $NH_2\text{-}(CH_2)_3\text{—}N[N+(O)N\text{—}OH)]\text{—}(CH_2)_4\text{—}NH\text{—}(CH_2)_3\text{—}NH_2$. SDD is manufactured by Molecular Probes, Inc., Eugene, Oreg. Alternatively, other diazenium diolate-type NO donors can be used. One example of a suitable diazenium diolatetype NO donor is 1-{N-methyl-N-[6-(N-methylammonio)hexyl]amino}diazen-1-ium-1,2-diolate having the formula $CH_3\text{—}N+H_2\text{—}(CH_2)_6\text{—}N(CH_3\text{—}N+(O\text{—})\text{=}N\text{—}O\text{—}$ (MAHMA-NO). Another example of a suitable alternative NONOate is and Z-1-[N-(2-aminoethyl)-N-(2-ammonioethyl)amino]diazen-1-ium-1,2-diolate having the formula $O\text{—}N+[N(CH_2\text{—}CH_2\text{—}NH_2)CH_2\text{—}CH_2\text{—}N+H_3]\text{=}N\text{—}O\text{—}$ (DETA-NO). MAHMA-NO and DETA-NO can be obtained from Cayman Chemical Co., Ann Arbor, Mich.

Examples of polycationic peptides that can be used to make B-units include poly(L-arginine), poly(D-arginine), poly(D,L-arginine), poly(L-lysine), poly(D-lysine), poly(δ-guanidino-α-aminobutyric acid), and a racemic mixture of poly(L-arginine) or poly(D-arginine). The terms "poly(L-arginine)", "poly(D-arginine)", "poly(D,L-arginine)" includes L-, D-, and/or D,L-arginine in both its polymeric and oligomeric form.

Heparin derivates can be used for the B-units, as well. Heparin is derived from a mixture of sulfated polysaccharide chains based on D-glucosamine and D-glucoronic or L-iduronic acid. In some embodiments, "heparin derivative" include any functional or structural variation of heparin. Representative variations include heparinoids, heparin having a hydrophobic counterion, heparan sulfate, alkali metal or alkaline-earth metal salts of heparin, for example, sodium heparin (also known as hepsal or pularin), potassium heparin (formerly known as clarin), lithium heparin, calcium heparin (also known as calciparine), magnesium heparin (also known as cutheparine), low molecular weight heparin (also known as ardeparin sodium), and blends thereof. Alternatively, some embodiments define "heparin derivatives" to specifically exclude any one or any combination of heparinoids, heparin having a hydrophobic counterion, heparan sulfate, alkali metal or alkaline-eartlh metal salts of heparin, sodium heparin (also known as hepsal or pularin), potassium heparin (formerly known as clarin), lithium heparin, calcium heparin (also known as calciparine), magnesium heparin (also known as cutheparine), or low molecular weight heparin (also known as ardeparin sodium).

Examples of other B-unit-suitable polysaccharides include glycosaminoglycans (or mu-copolysaccharides) such as keratan sulfate, chondroitin sulfate, dermatan sulfate (also known as chondroitin sulfate B), hyaluronic acid, hyaluronates and blends thereof.

The acrylate moiety forming a part of the random or block copolymer (A- and/or C-units shown in Formula II) can be derived from $CH_2\text{=}CX\text{-}M$ acrylates. For example, any monomer shown in Table 1 can be used.

The biobeneficial moiety forming the random or block copolymer (B-units in Formula II) from unsaturated monomers or oligomers. The choice of the monomer or oligomer depends on the desired biological response. For example, the biobeneficial moiety can be anti-restenotic or can ensure better blood compatibility, or can promote cell adhesion.

Examples of the monomers or oligomers yielding antirestenotic moieties can be derived include acryloyl-, methacryloyl-, vinyl or allyl-modified adducts of SODm, acryloyl-, methacryloyl-, vinyl or allyl-modified NO donors examples of NO donors include DETA or speramine), acryloyl-, methacryloyl-, vinyl or allyl-modified adducts of phosphoryl choline, and acryloyl-, methacryloyl-, vinyl or allyl-modified polycationic peptides such as poly-L-arginine.

Examples of monomers that can form the biobeneficial moiety include 2-acrylamido-2-methyl-1-propanesulfonic acid, poly(ethylene glycol)methacrylate, 3-sulfopropyl acrylate, 3-sulfopropyl methacrylate, N-vinylpyrrolidone, vinylsulfonic acid, 4-styrenesulfonic acid and 3-allyloxy-2-hydroxypropanesulfonic acid. All monomers based on sulfonic acid can be either alkali metal salts (e.g., K+ or Na+) or acids.

Turning again to the polymeric structure represented by Formula II, some examples of particular copolymers having that structure that can be used include poly(ethylene glycol)-block-poly(n-butylmethacrylate)-block-poly(ethylene glycol) (PEG-PBMA-PEG, an ABA block co-polymer), or poly(n-butylmethacrylate)-block-poly(ethylene glycol)-block-poly(n-butylmethacrylate) (PBMA-PEG-PBMA, a BAB-block copolymer). In both PEG-PBMA-PEG and PBMA-PEG-PBMA, the molecular weight of the PEG units can be between about 500 and 30,000 Daltons, and the molecular weight of the PBMA units can be between about 500 and 30,000 Daltons.

The random or block copolymers represented by Formula II can be obtained by common synthetic methods, for example, by radical copolymerization of monomers forming A-, B-, and/or C-units in bulk, solution, suspension, or emulsion with of suitable initiators.

For preparing random copolymers, standard radical-polymerization initiators can be used. Examples of suitable initiators include azobis(isobutyronitrile) and 2,2-dimethoxy-2-phenol acetophenone. Optionally, the photosensitizer, benzophenone, can be added to 2,2-dimethoxy-2-phenol acetophenone.

Living, free-radical copolymerization followed by initiation-transfer-agent termination of the living polymer chains (the inferter process) can yield inventive block copolymers. The inferter process uses an initiator that exhibits thermal photolytic free-radical decomposition. Examples of these initiators are benzyl-N,N-diethyldithiocarbamate (BDC) or p-xylylene-N,N-diethyldithiocarbamate (XDC). BDC is a toluene derivative and has the formula shown in Formula III:

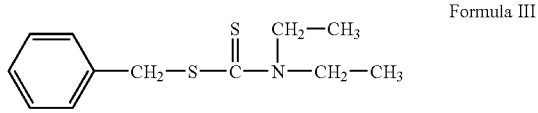

Formula III

XDC is a p-xylene derivative and has the formula shown in Formula IV:

an anhydrous methanol solution. Some embodiments use an equimolar or substantially equimolar ratio. The mixture can be stirred for about 24 hours at about room temperature to yield BDC solution. The solution can be removed by evaporating methanol at a reduced pressure or by vacuum distillation. The synthesis of XDC is similar, except, α,α-dibromo-p-xylene replaces benzyl bromide, and the molar ratio between sodium N,N-diethyldithiocarbamate and α,α-dibromo-p-xylene can rise to about 1:2.3. This yields XDC, which can be purified by recrystallization in methanol.

Optional Component

In some embodiments, other polymers can be added to composition. This can be in a form of a simple blend or a linking, conjugation or bonding process. Representative examples include poly(ethylene-co-vinyl alcohol), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), poly(glycerol-sebacate), polyphosphoester, polyphosphoester urethane; poly(amino acids), cyanoacrylates, poly(trimethylene carbonate), poly(iminocarbonate), copoly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, other polycarbonates, polyoxymethylenes, polyimides, polyethers, epoxy resins, other polyurethanes, rayon, rayon-triacetate, cellulose, cellulose acetate, cellulose butyrate, cellulose acetate butyrate, cellophane, cellulose nitrate, cellulose propionate, cellulose ethers, soluble fluorinated polymers and carboxymethyl cellulose.

In addition to or in lieu of another polymer, a drug or therapeutic agent can serve as the optional component. The therapeutic agent can include any substance capable of exerting a therapeutic, diagnostic or prophylactic effect for a patient. The therapeutic agent may include small molecules, peptides, proteins, oligonucleotides, and the like. The therapeutic agent could be designed, for example, to inhibit the vascular-smooth-muscle-cell activity. It can inhibit abnormal or inappropriate migration or proliferation of smooth muscle

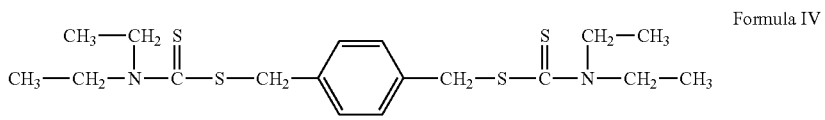

Formula IV

BDC or XDC initiators can be synthesized by combining sodium N,N-diethyldithiocarbamate with benzyl bromide in cells. Examples of therapeutic substances that can be used include antiproliferative substances such as actinomycin D, or derivatives and analogs thereof (manufactured by Sigma-Aldrich of Milwaukee, Wis., or COSMEGEN available from Merck). Synonyms of actinomycin D include actinomycin, actinomycin IV, actinomycin I1, actinomycin X1, and actinomycin C1. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany), methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycing from Bristol-Myers Squibb Co., Stamford, Conn.). Examples of antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

Medial Device Application

A medical device can be made from the composition or coated with the composition. The device can include any medical device, preferably implantable medical devices such as catheters, balloons, guidewires, stents, grafts, stent-grafts, intra-ocular lenses, artificial heart valves, cerebrospinal fluid shunts, pacemaker electrodes, and endocardial leads. The underlying structure of the device can be of virtually any design. The device can be made of a metallic material or an alloy such as, but not limited to, cobalt chromium alloy (EL-GILOY), stainless steel (316L), "MP35N," "MP20N," ELASTINITE (Nitinol), tantalum, nickel-titanium alloy, platinum-iridium alloy, gold, magnesium, or mixtures thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In one example, the device is a bioabsorbable or erodable stent.

Stents

The embodiments of the present invention can be used as a coating for a stent. The stent can include a primer layer; a drug-polymer layer (also referred to as "reservoir" or "reservoir layer") or alternatively a polymer-free drug layer; a topcoat layer; and a finishing coat layer. The top coat layer or the primer layer can be free from any drugs. Some drugs may migrate into these layers during or subsequent to the manufacturing process. Any one or combination of the coating layers can be formed on the stent by dissolving the composition of the present invention in a solvent, or a solvent mixture, and applying the solution to the stent by spraying or immersion. The removal of the solvent can produce a dry coating. Elevating the temperature can accelerate drying. The complete coating can be annealed between about 40 and about 150° C. for about 5 to about 60 minutes, if desired, to improve the coating's thermal stability. To incorporate a drug into the reservoir layer, the drug can be combined with the polymer solution.

A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

The compositions of the invention can be used for the treatment of a variety of disorder in mammals including atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, cancer as well as other disorders.

Embodiments of the present invention are further illustrated by the following examples. Throughout the examples section and throughout the specification and claims, for economy of language "solvent" means pure solvents and systems of mixtures of solvents.

EXAMPLE 1

Synthesis of a Random Copolymer

A solution comprising a blend of monomers, a thermal initiator, and a solvent can be prepared by thoroughly mixing the following components:

(a) about 25 mass % of a first monomer, methylmethacrylate (MMA);

(b) about 19 mass % of a second monomer, n-butyl-methacrylate (BMA);
(c) about 8 mass % of a third monomer, poly(ethylene glycol)-methacrylate (PEGMA), where PEG can have weight-average molecular weight of about 6,000;
(d) between about 0.5 mass % and about 3.0 mass %, for example, about 1.5 mass % of a thermal initiator, azobis-isobutyronitrile (AIBN); and
(e) the balance of a solvent such as benzene.

AIBN is an example of a useful thermal initiator. Those having ordinary skill in the art know of others, for example, peroxide-type initiators, as well.

Thermal radical copolymerization can be carried between about 50 and about 60° C. for an amount of time, for example, for about 2 hours. The process can be carried out in an inert atmosphere, such as that created by bubbling an inert gas such as nitrogen or argon through the solution for about 30 minutes. At 50-60° C., AIBN decomposes, releasing nitrogen and generating free radicals.

These free radicals then react with MMA, BMA, and PEGMA that are present in the blend, initiating and propagating radical copolymerization, yielding a random copolymer, poly(methyl methacrylate-co-n-butyl methacrylate-co-poly(ethylene glycol)-methacrylate) or P(MMA-BMA-PEGMA). One possible structure of P(MMA-BMA-PEGMA) is shown by Formula V:

The solution of BMA and XDC in 2-butanone can be placed into a borosilicate vial, purged with dry nitrogen for about 30 minutes, and the vial can be sealed. The contents can be UV irradiated at a wavelength of about 310 and about 400 nm, for about 12 hours. The vial can then be opened, and the contents can be added dropwise to ethanol −76° C. As a result, poly(butylmethacrylate)-XDC adduct (PBMA-XDC) can be precipitated, collected, and vacuum dried using a vacuum funnel.

Next, PBMA-XDC can be combined with acryloyl poly (ethylene glycol) (acryloyl-PEG) and 2-butanone in the amounts shown in Table 3.

TABLE 3

| No. | Component | Amount mmol | g |
|---|---|---|---|
| 1 | PBMA-XDC | 0.0064 | 1.00 |
| 2 | 2-butanone | — | 12.40 |
| 3 | Acryloyl-PEG | 0.625 | 0.25 |

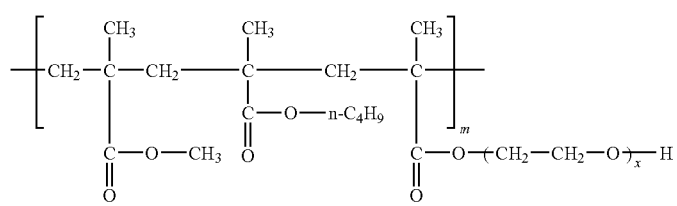

Formula V

Optionally, P(MMA-BMA-PEGMA) can be obtained with a UV-initiated process. To conduct this process, a solution comprising a blend of BMA, MMA and PEGMA in benzene can be prepared, as described above. A photoinitiator, e.g., 2,2-dimethoxy-2-phenol acetophenone, can be dissolved in the solution instead of AIBN. The amount of 2,2-dimethoxy-2-phenol acetophenone can be the same as described above. The solution can then be exposed to UV radiation at a wavelength of 360 nm while being stirred yielding P(MMA-BMA-PEGMA), Formula V.

EXAMPLE 2

Synthesis of an ABA-Block Copolymer

As a first step, n-butylmethacrylate (BMA) can be dissolved in 2-butanone and an initiator, XDC, can be added. Component amounts are summarized in Table 2.

TABLE 2

| No. | Component | Amount mmol | g |
|---|---|---|---|
| 1 | BMA | 140.700 | 19.98 |
| 2 | 2-butanone | — | 59.41 |
| 3 | XDC | 0.287 | 0.1151 |

Acryloyl-PEG is a PEG esterification product of acrylic acid and has a Formula VI:

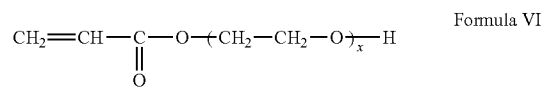

Formula VI

A low molecular weight acryloyl-PEG oligomer, with a number-average molecular weight (Mn) or about 375, can be used. This corresponds to a value of x in Formula VI of about 7. The blend of PBMA-XDC, acryloyl-PEG and 2-butanone can be UV irradiated at a wavelength of about 310 to about 400 nm, for about 12 hours. The vial can then be opened, and the contents can be added dropwise to water and vigorously stirred at about 70° C. for about 2 hours, evaporating the 2-butanone and suspending the poly(acryloyl-PEG)-block-n-butylmethacrylate-block-acryloyl-PEG)-XDC. The suspension can be cooled to room temperature, and the precipitate can be collected and vacuum dried using a vacuum funnel. The adduct is then hydrolyzed in the presence of a strong base to remove XDC. As a result, poly(acryloyl-PEG-block-n-butylmethacrylate-block-acryloyl-PEG) (PEG-PBMA-PEG), which is a ABA-block copolymer having Formula VII, can be precipitated.

Formula VII

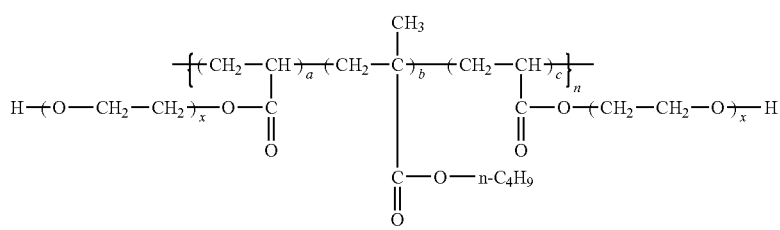

EXAMPLE 3

Synthesis of an AB Block Copolymer

First, a PBMA-XDC adduct can be obtained from Example 2. Second, PBMA-XDC can be combined with acryloyl poly (ethylene glycol) (acryloyl-PEG) and 2-butanone in the amounts shown in Table 4.

TABLE 4

| No. | Component | Amount | |
|---|---|---|---|
| | | mmol | g |
| 1 | PBMA-XDC | 0.0032 | 0.50 |
| 2 | 2-butanone | — | 12.40 |
| 3 | Acryloyl-PEG | 0.625 | 0.25 |

A low-molecular-weight acryloyl-PEG oligomer, with a number-average molecular weight (Mn) of about 375, can be used. This corresponds to a value of x in Formula VII of about 7. The blend of PBMA-XDC, acryloyl-PEG and 2-butanone can be UV radiated at a wavelength of about 310 to about 400 nm, for about 12 hours. The vial can then be opened, and the contents can be added dropwise to water and vigorously stirred at a about 70° C. for about 2 hours, evaporating the 2-butanone and suspending the poly(n-butylmethacrylate-block-acryloyl-PEG)-XDC. The suspension can be cooled to room temperature and the precipitate can be collected and vacuum-dried. The adduct is then hydrolyzed in the presence of a strong base to remove XDC, yielding poly(n-butyl-methacrylate-block-acryloyl-PEG) (PBMA-PEG), which is an AB-block copolymer having Formula VIII.

Formula VIII

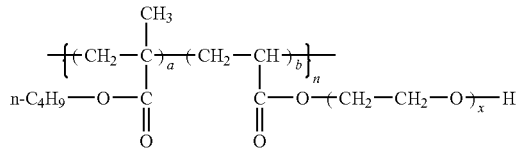

EXAMPLE 4

Synthesis of a Copolymer Containing Phosphoryl Choline Moiety

Equimolar amounts of n-butyl methacrylate (BMA), acryloyl-PEG, and acryloyl-phosphoryl choline can be mixed and dissolved in 2-butanone. Phosphoryl choline is also known as N,N,N-trimethyl-2-aminoethyl phosphonate. Acryloyl-phosphoryl cho-line is an acrylic derivative of phosphoryl choline having the Formula IX:

Formula IX

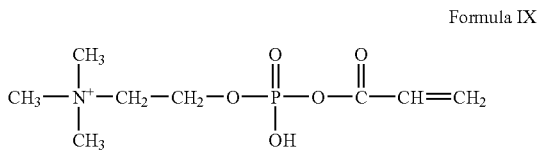

A low molecular weight acryloyl-PEG oligomer, with a number-average molecular weight (Mn) of about 375, can be used. This corresponds to a value of x in Formula X of about 7. The blend of BMA, acryloyl-PEG, acryloyl-phosphoryl choline and 2-butanone can be UV radiated at a wavelength of about 310 to about 400 nm, for about 12 hours. The vial can then be opened, and the contents can be added dropwise to water and vigorously stirred at a about 70° C. for about 2 hours, evaporating the 2-butanone and suspending the poly (n-butylmethacrylate-co-acryloyl-PEG-co-acryloyl-phosphoryl choline). The suspension can be cooled to the room temperature, and the precipitate can be collected and vacuum dried. As a result, poly(n-butylmethacrylate-co-acryloyl-PEG-co-acryloyl-phosphoryl choline) (PBMA-PEG-PC), can be obtained. One possible structure for PBMA-PEG-PC is shown by Formula X:

Formula X

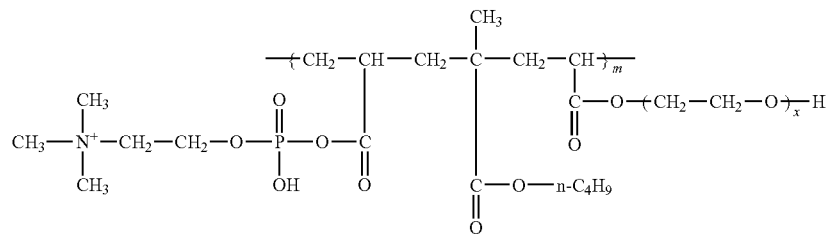

EXAMPLE 5

A first composition can be prepared by mixing the following components:
(a) about 2.0 mass % PBMA; and
(b) the balance, a solvent blend of acetone and cyclohexanone in a mass ratio of about 7:3.

The first composition can be sprayed onto the surface of a bare 13 mm TETRA stent (available from Guidant Corporation), and dried to form a primer layer. A spray coater can be used having a 0.014 fan nozzle maintained at about 60° C. with a feed pressure of about 0.2 atm (about 3 psi) and an atomization pressure of about 1.3 atm (about 20 psi). The primer layer can be baked at about 80° C. for about 30 minutes, yielding a dry primer layer. The dry primer layer can contain about 60 µg of PBMA.

A second composition can be prepared by mixing the following components:
(a) about 1.5 mass % PBMA;
(b) about 0.5 mass % PBMA-PEG block copolymer obtained as described in Example 3;
(c) about 1.0 mass % EVEROLIMUS; and
(d) the balance, DMAC as the solvent (alternatively, cyclohexanone can be used as the solvent).

Overall, the second composition can contain about 600 µg of the mixture. It composition can be applied onto the dried primer layer to form a reservoir layer, using the primer layer's spraying techniques and equipment. This is followed by drying, e.g., by baking at about 50° C. for about 2 hours, yielding a dry reservoir layer.

A third composition can be prepared by mixing the following components:
(a) about 2.0 mass % the PBMA-PEG block-polymer described in Example 3; and
(b) the balance, DMAC as the solvent (alternatively, cyclohexanone can be used as the solvent).

The third composition can be applied onto the dried reservoir layer to form a topcoat layer using the same spraying technique and equipment used for applying the primer layer and the reservoir layer. The wet topcoat layer can be dried and baked at about 50° C. for about 2 hours. The dry topcoat layer can contain about 200 µg of the PBMA-PEG block-polymer.

EXAMPLE 6

A primer layer can be fabricated as described in Example 5.
A first composition can be prepared by mixing the following components:
(a) about 1.5 mass % PBMA;
(b) about 0.5 mass % PBMA-PEG block copolymer obtained as described in Example 3;
(c) about 0.05 mass % PEG having molecular weight between about 4,000 and about 100,000 Daltons; (up to 0.06 mass % of this PEG can be used in this example)
(d) about 1.0 mass % EVEROLIMUS; and
(e) the balance, DMAC as the solvent (alternatively, cyclohexanone can be used as the solvent).

Overall, the second composition can contain about 600 µg of the mixture. It can be applied onto the dried primer layer to form the reservoir layer as described in Example 5.

A third composition can be prepared by mixing the following components:
(a) about 2.0 mass % the PBMA-PEG block-polymer described in Example 3; and
(b) the balance, DMAC as the solvent (alternatively, cyclohexanone can be used as the solvent).

The third composition can be applied onto the dried reservoir layer to form a topcoat layer as described in Example 5.

EXAMPLE 7

A primer layer can be fabricated as described in Example 5.
A first composition can be prepared by mixing the following components:
(a) about 1.5 mass % PBMA;
(b) about 0.5 mass % PBMA-PEG block copolymer obtained as described in Example 3;
(c) about 0.05 mass % PEG having molecular weight between about 4,000 and about 100,000 Daltons; (up to 0.06 mass % of this PEG can be used in this example)
(d) about 0.06 mass % Na heparin; (up to 2.5 mass % Na heparin)
(e) about 1.0 mass % EVEROLIMUS; and
(f) the balance, DMAC as the solvent (alternatively, cyclohexanone can be used as the solvent).

Overall, the second composition can contain a about 600 µg of the mixture. When Na heparin is used, the composition is not necessarily a solution because Na heparin is not completely soluble in the solvent. It can be applied onto the dried primer layer to form the reservoir layer as described in Example 5.

A third composition can be prepared by mixing the following components:
(a) about 2.0 mass % the PBMA-PEG block-polymer described in Example 3; and
(b) the balance, DMAC as the solvent (alternatively, cyclohexanone can be used as the solvent).

The third composition can be applied onto the dried reservoir layer to form a topcoat layer as described in Example 5.

EXAMPLE 8

A primer layer can be fabricated as described in Example 5.
A first composition can be prepared by mixing the following components:
(a) about 1.5 mass % PBMA;
(b) about 0.5 mass % PBMA-PEG block copolymer obtained as described in Example 3;
(c) about 0.05 mass % PEG having molecular weight between about 4,000 and about 100,000 Daltons; (up to 0.06 mass % of this PEG can be used in this example)
(d) about 0.06 mass % hydrophobic quaternized heparin; (up to 2.5 mass % hydrophobic quaternized heparin)
(e) about 1.0 mass % EVEROLIMUS; and
(f) the balance, DMAC as the solvent (alternatively, cyclohexanone can be used as the solvent).

Overall, the second composition can contain a about 600 µg of the mixture. It can be applied onto the dried primer layer to form the reservoir layer as described in Example 5.

A third composition can be prepared by mixing the following components:
(a) about 2.0 mass % the PBMA-PEG block-polymer described in Example 3; and
(b) the balance, DMAC as the solvent (alternatively, cyclohexanone can be used as the solvent).

The third composition can be applied onto the dried reservoir layer to form a topcoat layer as described in Example 5.

EXAMPLE 9

A primer layer and a reservoir layer can be fabricated as described in Example 5.

A composition can be prepared by mixing the following components:

(a) about 2.0 mass % POLYACTIVE copolymer; and
(b) the balance, a solvent blend of 1,1,2-tricloroethane and chloroform in a mass ratio between 1,1,2-tricloroethane and chloroform of about 4:1.

POLYACTIVE is a trade name of a family of poly(ethylene glycol)-block-poly(butyleneterephthalate)-block poly(ethylene glycol) copolymers (PEG-PBT-PEG) and is available from IsoTis Corp. of Holland. The grade of POLYACTIVE that can be used can have about 45 molar % units derived from PBT and about 55 molar % units derived from PEG. The molecular weight of the PEG units can be about 300 Daltons. The overall weight-average molecular weight (Mw) of POLYACTIVE can be between about 75,000 Daltons and about 125,000 Daltons.

The composition can be applied onto the dried reservoir layer to form a topcoat layer as described in Example 5.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical article comprising an implantable medical device and a coating deposited on at least a part of the device, the coating including:
   (a) a structural component comprising a linear acrylic homopolymer or linear acrylic copolymer; and
   (b) a biobeneficial component comprising a poly(ethylene glycol)-poly(n-butylmethacrylate)-poly(ethylene glycol) block copolymer having an acrylate moiety and a biobeneficial moiety.

2. The medical article of claim 1 wherein the implantable medical device is a stent.

3. The medical article of claim 1 wherein the mass ratio between the structural component and the biobeneficial component is between about 99:1 and about 1:1.

4. The medical article of claim 1 wherein the mass ratio between the structural component and the biobeneficial component is between about 19:1 and about 9:1.

5. The medical article of claim 1 wherein the mass ratio between the structural component and the biobeneficial component is about 3:1.

6. The medical article of claim 1 wherein the acrylic homopolymer and linear acrylic copolymer have the structure:

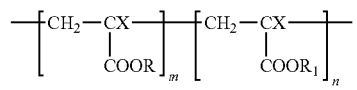

wherein
(a) X is hydrogen or methyl group;
(b) each of R and $R_1$ is independently methyl, ethyl, n-propyl, iso-propyl, n-butyl, sec-butyl, iso-butyl, tert-butyl, lauryl, or 2-hydroxyethyl;
(c) m is a positive integer; and
(d) n is 0 or a positive integer.

7. The medical article of claim 1 wherein the acrylic homopolymer or linear acrylic copolymer are poly(methylmethacrylate), poly(ethylmethacrylate), poly(n-propyl methacrylate), poly(iso-propylmethacrylate), poly(n-butylrnethacrylate), poly(n-laurylmethacrylate), poly(2-hydroxyethylmethacrylate), poly(methylmethacrylate-co-2-hydroxyethyl methacrylate), poly(n-butylmethacrylatc-co-2-hydroxyethyl methacrylate), or mixtures thereof.

8. The medical article of claim 1 wherein the biobeneficial moiety is from poly(alkylene glycols), superoxide dismutate-mimetics (SODm), diazenium diolate type nitric oxide donors, polycationic peptides, polysaccharides, pyrrolidone, vitamin E, sulfonated dextrase, β-phenoxyethanol, N,N-dimethylamino-2-ethanol, mannose-6-phosphate, sulfonic acid, derivatives of sulfonic acid, or mixtures thereof.

9. The medical article of claim 8 wherein the poly(alkylene glycols) are poly(ethylene glycol), poly(propylene glycol), poly(tetramethylene glycol), poly(ethylene glycol-co-propylene glycol), poly(ethylene oxide-co-propylene oxide), or mixtures thereof.

10. The medical article of claim 1 wherein the mass ratio between the acrylate moiety and the biobeneficial moiety is between about 99:1 and about 1:1.

11. The medical article of claim 1 wherein the mass ratio between the acrylate moiety and the biobeneficial moiety is between about 19:1 and about 9:1.

12. The medical article of claim 1 wherein the mass ratio between the acrylate moiety and the biobeneficial moiety is about 3:1.

* * * * *